Figure 1:
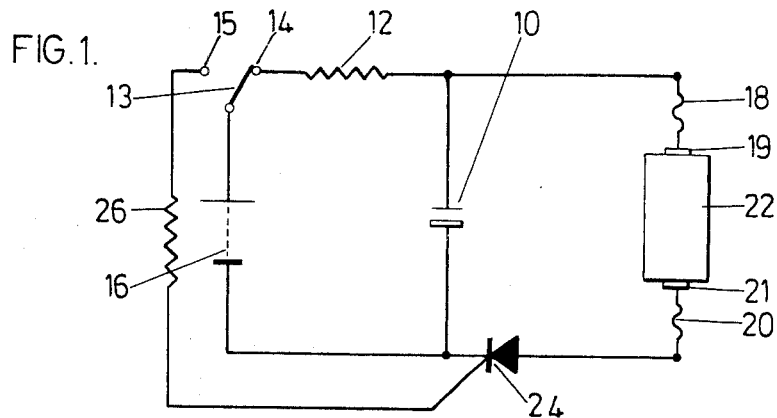

United States Patent [19]
Minchom

[11] 3,961,244
[45] June 1, 1976

[54] MAGNETIZING MEANS FOR A MAGNETIC FLAW DETECTOR INCLUDING A CHARGING AND DISCHARGING CIRCUIT

[75] Inventor: Raphael Isaac Minchom, London, England

[73] Assignee: Minchom Magnetic Systems Limited, London, England

[22] Filed: Sept. 11, 1974

[21] Appl. No.: 505,047

[52] U.S. Cl. .................................. 324/38; 320/1
[51] Int. Cl.² .................................. G01R 33/12
[58] Field of Search ............... 324/38, 117; 320/1; 219/113; 340/253 P; 317/80; 307/252 J; 328/67

[56] References Cited
UNITED STATES PATENTS

| | | | |
|---|---|---|---|
| 2,136,375 | 11/1938 | DeForest | 324/38 |
| 2,158,409 | 5/1939 | DeForest et al. | 324/38 |
| 2,312,083 | 2/1943 | Doane | 324/38 |
| 2,562,434 | 7/1951 | Oram | 324/133 |
| 3,134,048 | 5/1964 | Wolfframm et al. | 328/67 |
| 3,436,514 | 4/1969 | Broomhall et al. | 320/1 |
| 3,449,663 | 6/1969 | Schroeder et al. | 324/38 |

FOREIGN PATENTS OR APPLICATIONS

| | | | |
|---|---|---|---|
| 834,256 | 11/1938 | France | 324/38 |
| 125,075 | 3/1959 | U.S.S.R. | 324/37 |

Primary Examiner—Robert J. Corcoran
Attorney, Agent, or Firm—Cushman, Darby & Cushman

[57] ABSTRACT

This invention concerns a method for magnetically detecting flaws in a magnetisable object, comprising charging at least one storage capacitor from a D.C. power source, generating magnetic flux in the object by discharging the capacitor, and applying magnetisable particles to the object to indicate the magnetic flux whereby to indicate the flaws.

11 Claims, 7 Drawing Figures

MAGNETIZING MEANS FOR A MAGNETIC FLAW DETECTOR INCLUDING A CHARGING AND DISCHARGING CIRCUIT

This invention relates to a method of and apparatus for detecting flaws in magnetisable objects.

According to the present invention there is provided apparatus for magnetically detecting flaws in a magnetisable object, the said apparatus comprising a first circuit having a storage capacitor therein and adapted to be connected across a D.C. power source; a second circuit comprising the said storage capacitor, a thyristor, and permanent magnet connector means for electro-magnetically connecting the storage capacitor to the object; a third circuit comprising the said thyristor and adapted to be connected across the said D.C. power source; and a multi-position switch connected in both the first and third circuits, the switch having a first position in which the second and third circuits are open-circuited and in which the first circuit is completed to effect charging of the storage capacitor by the D.C. power source, and the switch having a second position in which the first circuit is open-circuited and the third circuit is closed, such closure of the third circuit causing the thyristor to close the second circuit whenever a said object is connected to the connector means and thus causing the storage capacitor to be discharged and to generate magnetic flux in the object.

The apparatus may comprise a D.C. power source for charging the storage capacitor, said D.C. power source being a dry cell or cells, e.g., of high capacity.

The connector means may each comprise two conductors each of which may have a permanent magnet for attaching the conductor to the object or to the magnetisable structure by magnetic force. The total resistance of the conductors preferably does not exceed 20 milliohms.

The connector means may be such that discharge of the capacitor aids the magnetic forces between the permanent magnets and the object of the magnetisable structure.

Each permanent magnet may have a recess with a resilient member disposed therein, each permanent magnet being arranged to urge the conductor into contact with the object or magnetisable structure.

Each conductor may comprise a compressible material, for example braided wire.

Each conductor may be insulated from the permanent magnet. Means may be provided for detecting current flow through a said conductor.

The apparatus may comprise a magnetisable core adapted to have the object connected between its ends to form a magnetic circuit, an inductor for magnetising the core, and terminals connected to the coil and adapted to receive the connector means.

Figure 2:
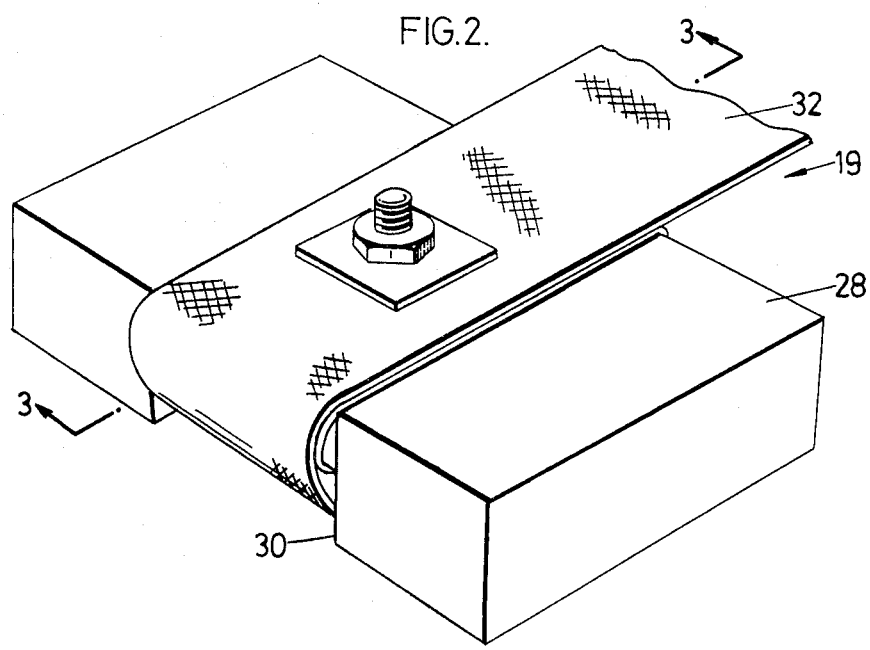
Figure 3:
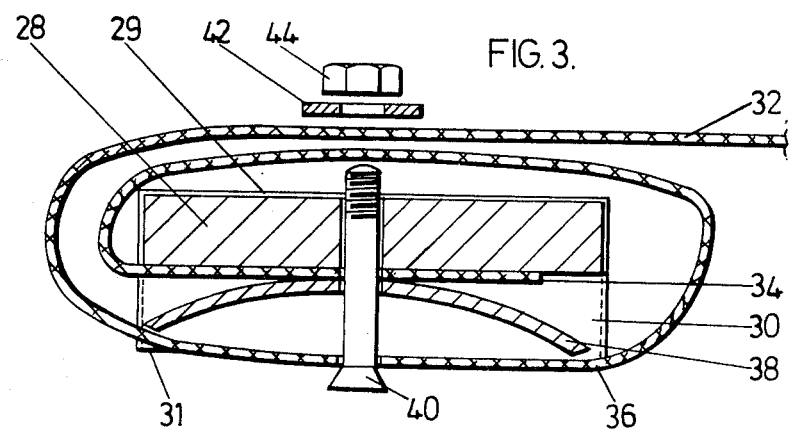
Figure 4:
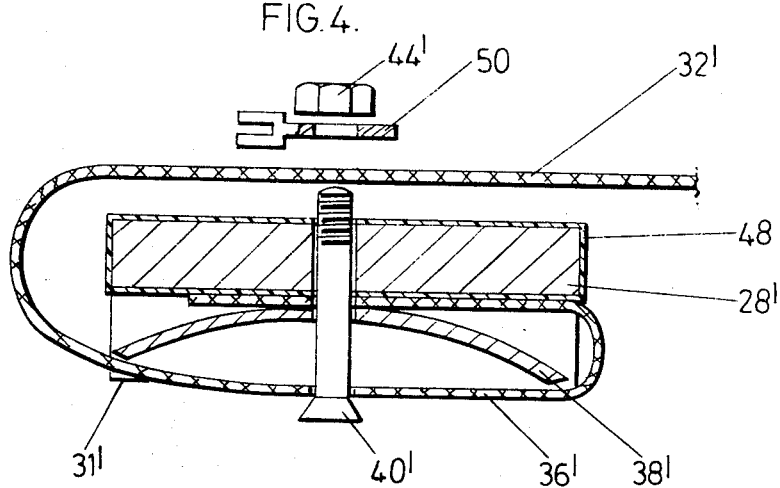
Figure 6:
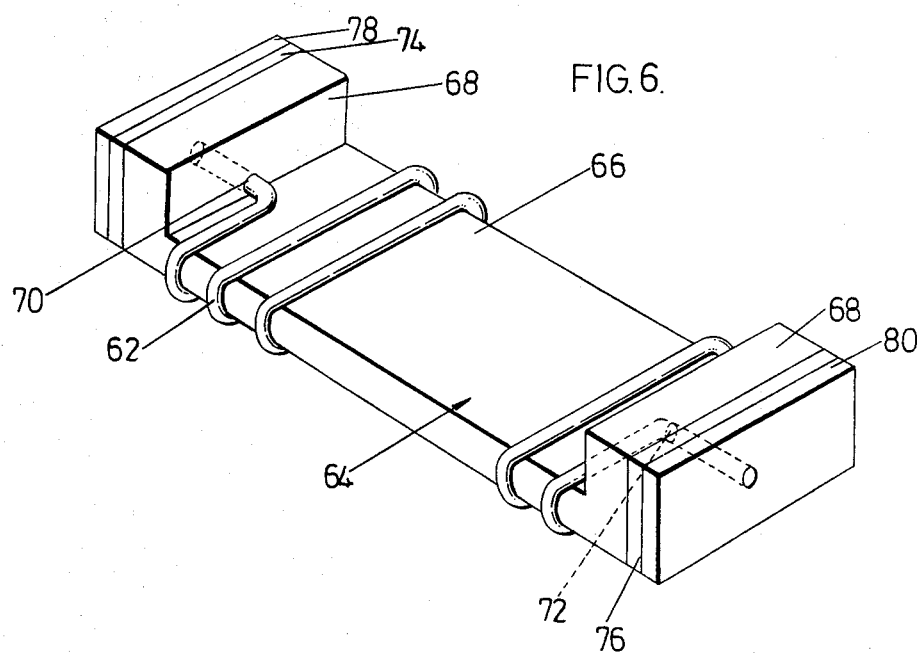
Figure 7:
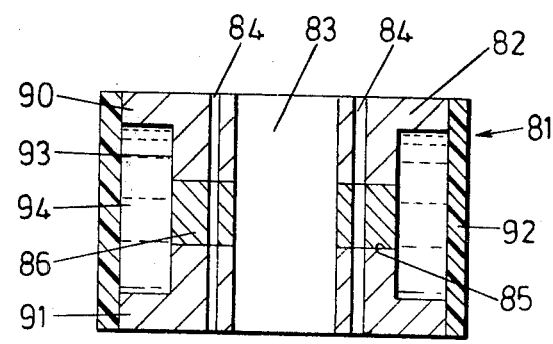
Figure 5:
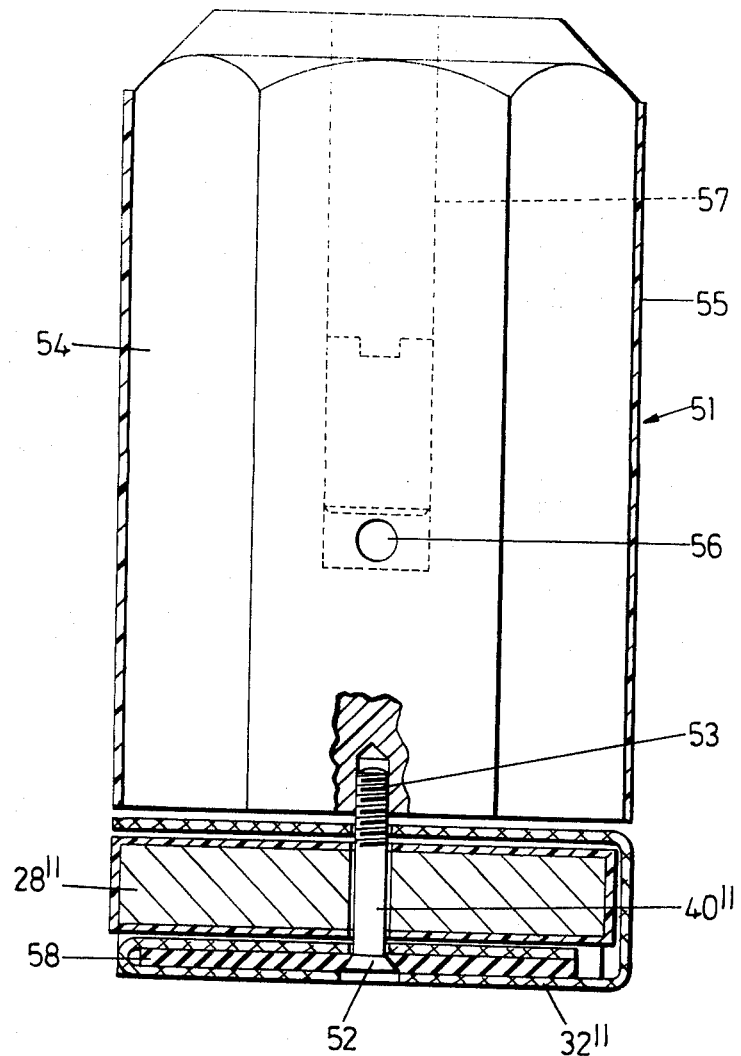

The invention will be described, merely by way of example, with reference to the accompanying drawings, wherein FIG. 1 is a circuit diagram of apparatus according to the invention, FIG. 2 is a perspective view of part of the apparatus of FIG. 1, FIG. 3 is a section of the plane 3—3 of FIG. 2, FIG. 4 is a similar section through an alternative embodiment of the apparatus shown in FIG. 2, FIG. 5 is a section similar to that of FIGS. 3 and 4 but showing yet another embodiment, FIG. 6 is a perspective view of another part of the apparatus of FIG. 1, and FIG. 7 is a sectional view of a current flow detector which may be used in the circuit shown in FIG. 1.

A technique used in the detection of internal flaws in a magnetisable object comprises generating magnetic flux in the object and applying magnetisable particles such as iron filings to the surface of the object. The particles distribute themselves along the lines of magnetic flux in the object, and interruptions in these lines of flux caused by a flaw are rendered visible. The flux is generated either by passing a heavy current (e.g. between 500 and 6,000 amps) through the object, or by placing the object within a large magnetising coil. Hitherto, the heavy current required in either case has been provided by means of a transformer. However, suitable transformers are bulky (up to 60 Kg or more) and expensive, and in cases where the current is passed through the object to be tested, there is often some burning of the object where it is connected to the transformer. This burning may occur even if currentlimiting fuses are included in the circuit.

The illustrated embodiments of the present invention are intended to minimise the above disadvantages, and to provide a more compact apparatus which is easily portable. Broadly speaking, this is achieved by employing one or more storage capacitors instead of the transformer.

Referring to FIG. 1, this example of apparatus according to the invention comprises a first circuit in which there is connected a storage capacitor 10, or several capacitors connected together in parallel, having a total capacitance of between 20,000 and 60,000 microfarads. The first circuit also comprises a D.C. battery 16 from which the capacitor 10 is chargeable via a charging resistor 12 and a selectable contact 14 of a two-position switch 13. The battery 16 may have a potential of between 24 and 75 volts, and may consist of dry cells or secondary cells.

Connected to opposite ends of the capacitor 10 are wander leads 18, 20 forming part of a second circuit. The total resistance of the wander leads 18, 20 should be kept as low as possible and should preferably not exceed 20 milliohms. Indeed, it is preferred that this total resistance should not exceed 12 milliohms. These leads are provided at their free ends with connectors 19, 21 which may be connected either directly to an object 22 to be tested, or to an inductor of a magnetic structure in which the object to be tested may be incorporated to form a magnetic circuit. The connectors 19, 21 and the magnetic circuit and inductor will be discussed in detail later.

Connected in the second circuit is a thyristor 24 which is provided between the wander lead 20 and the capacitor 10, the control terminal of the thyristor being connected via a resistor 26 to another contact 15 of the two-position switch 13. The said control terminal, the resistor 26, the contact 15, and the battery 16 together form a third circuit.

When an object is to be tested for flaws, it either has the connectors 19, 21 attached directly to it, or otherwise it is incorporated in the magnetic structure and the connectors 19, 21 are connected to the inductor thereof. The capacitor 10 is then charged by closing the contact 14 as shown in FIG. 1, thereby closing the first circuit and so connecting the battery to the capacitor 10 via the charging resistor 12. At this stage, the said second and third circuits are open circuits. When the capacitor has charged, the switch 13 is then moved to its other position, in which the said first circuit is open-circuited so that the battery is connected from the capacitor. The said third circuit is however closed so that the switch 13 connects the battery via the contact 15 and the resistor 26 to the control terminal of the thyristor 24. The thyristor 24 is then gated to its conductive state so as to close the said second circuit, thus, permitting the capacitor 10 to discharge via the wander leads 18, 20 and either the object 22 or the inductor. The time constant of the circuit is such that the capacitor discharges quickly, producing a high current pulse (e.g. of 2,500 amps) of the same order of magnitude as would have been produced by a transformer.

In cases where the current pulse passes through the object, a circumferential magnetic field is generated therein so that when the surface of the object is sprayed with magnetisable particles it is usually possible to locate flaws which are in general parallel to the line of the current flow in the object. When the object forms part of a magnetic circuit, it is generally possible by spraying the object between its connections to the magnetic structure with magnetisable particles to locate flaws which are perpendicular to the magnetic lines of flux in the object. In either case the magnetisable particles may be applied before, simultaneously with or after the discharge of the capacitor. When the particles are applied after the discharge, the flux indicated is of course due to remanent permanent magnetism which has been induced in the object. The discharge can be repeated more than once if insufficient indication of the magnetic flux is induced in the object with a single discharge.

Depending on the overall resistance, capacitance and inductance of the system, which of course determines the time constant thereof, the current pulse may be in the form of a hyperbolic positive half wave.

There is a general relationship between the components of the circuit which can be expressed by the equation:

$$Rt/_{2L} = \log_e [(E/\hat{I})(\sqrt{C/L})]$$

where:
$t$ is the time taken in seconds for the current pulse to reach its maximum value,
$R$ is the overall resistance in ohms of the circuit,
$L$ is the overall inductance in henries,
$E$ is the charging voltage in volts,
$C$ is the capacitance in farads, and
$\hat{I}$ is the peak current in amperes.

We have found both by calculation and by tests that the time taken for the current pulse to reach its peak value is unlikely to be more than 20 microseconds. Even if it were greater in some circumstances, this time would probably still be too short to cause burning of the surface of the object in those cases where the connectors 19, 21 make contact with the object and the current passes through it.

Referring now to FIG. 2, there is shown in perspective the connector 19. The connector 21 is similar. The connector 19 consists of a permanent magnet 28 of generally rectangular section and which has a recess 30 provided in one face 31 thereof. The unrecessed portion of the magnet is insulated with a layer 29 of insulating tape. (See FIG. 3). Wrapped around the magnet 28 is the end of a length of braided copper wire 32, which forms the end of the wander lead 18. Indeed, the wander leads 18, 20 are preferably formed from a plurality of thicknesses of braided copper wire so as to reduce their resistance. The braided wire 32 is wrapped nearly twice around the permanent magnet 28, and passes along the recess 30. Thus, there are two layers 34, 36 (FIG. 3) of braided wire in the recess. Between these two layers is disposed a small leaf spring 38 having a naturally curved shape. A countersunk headed bolt 40 (e.g. of non-conductive nylon) passes through the layers of braided wire, through a hole in the leaf spring 38, and through a hole in the magnet 28. A washer and nut 42, 44 are provided so that the braided wire and the spring 38 are clamped to the magnet. The spring 38 forces the layer 36 of braided wire outwardly from the groove. It thus tends to project somewhat beneath the face 31 of the magnet. Consequently, when the magnet is applied to the object to be tested, or to the terminals of the inductor, the magnetic forces generated by the magnet pull the magnet against the surface of the object or the terminal, and compress the layer 36 of braided wire (which in itself is somewhat compressible and resilient) against the action of the spring 38. The layer 36 of the braided wire thus is forced into contact with the surface of the object or the inductor terminal, by the combined action of the magnetic forces of the magnet 28 and the elastic force due to the spring 38. This assists in forming a good electrical contact between the layer of braided wire 36 and the surface.

The arrangement shown in FIG. 2 is such that the current pulse also passes through the permanent magnet 28. Whilst this may not be disadvantageous, it is thought preferable that the magnet 28 should be insulated from the current-carrying parts. This is done in the arrangement shown in FIG. 4 wherein parts already described with reference to FIG. 3 have primed reference numerals. With reference to FIG. 4, the magnet 28' is covered with a layer of insulating material 48 on those parts likely to be contacted by the braided wire 32'. The surface 31' is not insulated. The braided wire 32' is not wrapped around the magnet to the same extent, although care is taken still to provide a layer 36' which can be forced into good contact with the surface of the object or the inductor terminal by the spring 38'. The threaded bolt 40' is of a non-conductive material such as, for example, nylon.

FIG. 4 also illustrates that, instead of employing a braided wire material for a substantial portion of the wander leads 18, 20, there can instead be provided only a short portion 32' of braided wire, just sufficient to be adequately wrapped around the magnet 28'. The remainder of the wander lead is then attached by a conventional tag connector to a terminal tag 50 which is secured by the nut and bolt 44', 40', so that it is in good contact with the upper surface of the portion of braided wire 32'.

By insulating the braided wire 32' from the magnet 28', and by wrapping it around the magnet to form a coil, the magnetic force of the magnet may be enhanced by the current pulse, provided the direction of the wrap (clockwise or anti-clockwise) is correctly related to the north and south poles of the magnet.

FIG. 5 shows a connector 51 which is generally similar to that of FIGS. 3 and 4 and which for this reason, will not be described in detail.

In the FIG. 5 construction, however, which employs a permanent magnet 28'', a leaf spring 38 or 38' is not used, while a countersunk headed bolt 40'' is employed whose head 52 is located between two thicknesses of braided copper wire 32″. A block 58 of rubber or other resilient insulating material is disposed between the two thicknesses of braided copper wire 32″. The upper end of the bolt 40″ has a threaded portion 53 which is screwed into an elongated nut 54 whose exterior is insulated with a layer 55 of plastics material. The nut 54 has a drilling 56 to receive the end of a lead (not shown), the said end extending into an axially extending passage 57 in the nut 54 and being clamped therein by a screw 58.

Referring to FIG. 6, there is shown a magnetisable structure to which the object to be tested may be attached in order to make a complete magnetic circuit. The structure comprises an inductor coil 62 and a ferromagnetic core 64. The inductor 62 consists of a large number of closely-wound turns (only a few are shown, and these are expanded for clarity), which are disposed upon cross-member 66 of the core 64. The core has upwardly projecting pole pieces 68 which give it a generally channel-section appearance. The inductor coil 62 is insulated from the core 64 and the ends of the coil pass through holes 70, 72 in the pole pieces 68 through insulating plates 74, 76 and are connected to ferromagnetic steel terminal plates 78, 80.

When an object is to be tested, it is placed in contact with and extending between the pole pieces 68, thus completing a magnetic circuit consisting of the object, the pole pieces 68 and the cross-member 66. The connectors 19, 21 are magnetically attached to the terminals 78, 80. Upon discharge of the capacitor 10, the current pulse induces magnetic flux in the magnetic circuit, and the lines of flux may be made visible by spraying the object (or that part disposed between the pole pieces 68) with magnetisable particles. As mentioned before, the particles may be applied before, during or after the discharge of the capacitors, and if necessary the capacitor may be charged and discharged more than once.

In FIG. 7 there is shown a current flow detector 81 which may be used in the circuit shown in FIG. 1 to indicate whether there has been a current flow through a wander lead 18, 20.

The current flow detector 81 comprises a soft iron member 82 of generally cylindrical shape having low remanent magnetism. The member 82 has an axial hole 83 therethrough to enable a wander lead 18, 20 to be passed therethrough. The member 82 also has two diametrically spaced apart axial drillings 84 therethrough.

The member 82 has a transverse hole 85 which is plugged with a plug 86.

The member 82 has end flanges 90, 91 which are sealed to and within a transparent sleeve 92 e.g. of "Perspex" (Registered Trade Mark). The transparent sleeve 92 and flanges 90, 91, together with an outer wall 93 of the member 82, define an annular recess 94. Within the annular recess 94 there is a liquid such as paraffin containing a small quantity of steel or other magnetisable metal particles.

When a wander lead 18, 20 is passed through the hole 83 and the circuit shown in FIG. 1 is used, the current pulse through the wander lead 18, 20, will magnetise the member 82 with the result that the steel particles will form two axial lines on the wall 93 which are aligned with the drillings 84. Because of the low remanent magnetism of the member 82, however, the steel particles will, after a short time no longer be held in lines against the wall 93. If desired, this dispersal of the steel particles can be expedited by effecting reverse magnetisation of the member 82.

Thus, in use, the presence or absence of the lines of steel particles on the wall 93 will indicate whether or not there has been a current flow through the wander lead.

The illustrated embodiments of the invention can provide a magnetic flaw testing apparatus which is more easily portable than a known apparatus including a mains-powered transformer. It also does not need a source of mains electricity or the connecting leads for such a supply.

I claim:

1. Apparatus for magnetically detecting flaws in a magnetisable object, the said apparatus comprising a first circuit having a storage capacitor therein and adapted to be connected across a D.C. battery; a second circuit comprising a series circuit including the said storage capacitor, a thyristor, and two conductors each extending to a permanent magnet and wound about said magnet, said magnet magnetically connecting said conductors and the storage capacitor to the object; a third circuit comprising the said thyristor and adapted to be connected across the said D.C. battery; and a multi-position switch connected in both the first and third circuits, the switch having a first position in which the second and third circuits are open-circuited and in which the first circuit is completed to effect charging of the storage capacitor by the D.C. battery, and the switch having a second position in which the first circuit is open-circuited and the third circuit is closed, such closure of the third circuit causing the thyristor to close the second circuit whenever said object is connected between the conductors, and thus causing the storage capacitor to be hyperbolically discharged and to generate magnetic flux in the object.

2. Apparatus as claimed in claim 1 in which the total resistance of the conductors does not exceed 20 milliohms.

3. Apparatus as claimed in claim 1 in which each conductor comprises a compressible material.

4. Apparatus as claimed in claim 1 in which each conductor is insulated from its permanent magnet.

5. Apparatus as claimed in claim 1 comprising means for detecting current flow through one of said conductors.

6. Apparatus as claimed in claim 1 in which each permanent magnet has a recess therein, a conductor disposed in said recess, and a resilient member which is disposed in said recess and which urges the conductor outwardly of the recess, application of the permenent magnet to said object causing the conductor to be compressed against the resilient member.

7. Apparatus as claimed in claim 6 in which the conductor is wrapped about the permanent magnet so as to have a plurality of turns in said recess.

8. Apparatus as claimed in claim 1 in which one of said conductors is disposed adjacent to a magnetisable member, the magnetisable member having at least one aperture therein, a transparent member, the magnetisable member defining with the transparent member a chamber the interior of which can be seen through the transparent member, and magnetisable particles in said chamber which, when a current passes through the conductor, become aligned with the said at least one aperture.

9. Apparatus as claimed in claim 8 in which the conductor passes through a hole in the magnetisable member, the said aperture being a drilling spaced from said hole.

10. Apparatus as claimed in claim 8 in which the magnetisable particles are dispersed in a liquid in said chamber.

11. Apparatus for magnetically detecting flaws in a magnetisable object, said apparatus comprising: a first circuit having a storage capacitor therein and adapted to be connected across a D.C. battery; a second circuit comprising a series circuit including said storage capacitor, a thyristor, and two conductors each extending to a permanent magnet and wound about said magnet; a magnetisable core adapted to have the object connected between its ends to form a magnetic circuit, an inductor coil for magnetising the core, terminals connected to the inductor coil and adapted to be contacted by the permanent magnets, said permanent magnets magnetically connecting said conductors and the storage capacitor to said inductor coil; a third circuit comprising said thyristor and adapted to be connected across said D.C. battery; and a multi-position switch connected in both first and third circuits, the switch having a first position in which the second and third circuits are open circuited and in which the first circuit is completed to effect charging of the storage capacitor by the D.C. battery, and the switch having a second position in which the first circuit is open circuited and a third circuit is closed, said closure of the third circuit causing the thyristor to close the second circuit whenever said inductor coil is connected between the conductors thus causing the storage capacitor to be discharged and to generate a magnetic flux in the magnetisable core and in the object.

* * * * *